(12) United States Patent
Herrig et al.

(10) Patent No.: US 11,602,575 B2
(45) Date of Patent: Mar. 14, 2023

(54) ACCUMULATOR APPARATUS FOR USE IN STERILIZATION

(71) Applicant: Medivators Inc., Minneapolis, MN (US)

(72) Inventors: Judson A. Herrig, Elko New Market, MN (US); Isaac Odim, Minneapolis, MN (US)

(73) Assignee: Medivators Inc., Minneapolis, MN (US)

( * ) Notice: Subject to any disclaimer, the term of this patent is extended or adjusted under 35 U.S.C. 154(b) by 345 days.

(21) Appl. No.: 16/849,003

(22) Filed: Apr. 15, 2020

(65) Prior Publication Data

US 2020/0330635 A1 Oct. 22, 2020

Related U.S. Application Data

(60) Provisional application No. 62/835,608, filed on Apr. 18, 2019.

(51) Int. Cl.
*A61L 2/26* (2006.01)
*A61L 2/18* (2006.01)

(52) U.S. Cl.
CPC .................. *A61L 2/26* (2013.01); *A61L 2/18* (2013.01); *A61L 2202/121* (2013.01); *A61L 2202/15* (2013.01); *A61L 2202/18* (2013.01); *A61L 2202/24* (2013.01)

(58) Field of Classification Search
CPC ........ A61L 2/26; A61L 2/18; A61L 2202/121; A61L 2202/15; A61L 2202/18; A61L 2202/24
See application file for complete search history.

(56) References Cited

U.S. PATENT DOCUMENTS

| | | | |
|---|---|---|---|
| 6,365,103 B1 * | 4/2002 | Fournier | A61L 2/202 422/116 |
| 6,977,061 B2 * | 12/2005 | Lin | A61L 2/14 422/297 |
| 2004/0062692 A1 * | 4/2004 | Lin | A61L 2/07 422/292 |

* cited by examiner

*Primary Examiner* — Sean E Conley (57) ABSTRACT

A decontamination system for a device, such as a lumen device, is provided. The decontamination system includes a terminal package defining a device receiving area. The terminal package includes a fluid inlet through which sterilant fluid can be delivered to the device receiving area. An accumulator apparatus is provided that is configured to switch between trapping sterilant fluid delivered into the device receiving area and delivering sterilant fluid to the device receiving area based on pressure changes in the device receiving area.

3 Claims, 8 Drawing Sheets

ACCUMULATOR APPARATUS FOR USE IN STERILIZATION

PRIORITY CLAIM

This application claims priority to and benefit of U.S. Provisional Application with Ser. No. 62/835,608 filed Apr. 18, 2019, entitled ACCUMULATOR APPARATUS FOR USE IN STERILIZATION, which is herein incorporated by reference in its entirety.

TECHNICAL FIELD

This disclosure relates generally to decontamination of medical devices; in particular, this disclosure relates to an accumulator device for delivering sterilant fluid in a decontamination system.

BACKGROUND

Robust medical instruments are often sterilized at high temperatures. Commonly, the instruments are sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Endoscopes can also present problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

Existing decontamination systems require a direct connection between a terminal package and a mechanical pump to introduce sterilant fluid into the lumen(s) of a lumen device. These connections present complexity into the decontamination system. Also, these connections traverse the sterile barrier of the terminal package.

Therefore, a need exists that overcomes one or more of the disadvantages of present decontamination systems.

SUMMARY OF THE INVENTION

According to one aspect, this disclosure provides a decontamination system for a device, such as a lumen device. The decontamination system includes a terminal package defining a receiving area, such as a lumen device receiving area. The terminal package includes a fluid inlet through which sterilant fluid can be delivered to the device receiving area. The system includes an accumulator apparatus configured to switch between trapping sterilant fluid delivered into the device receiving area and delivering sterilant fluid to the device receiving area based on pressure changes in the lumen device receiving area.

According to another aspect, this disclosure provides a terminal package for use in a decontaminating system. The terminal package includes a container dimensioned to receive a device, such as a lumen device, such that the container defines a receiving area, such as a lumen device receiving area. The container includes a fluid inlet defined in the container to deliver a sterilant fluid to the device receiving area. An accumulator apparatus is provided that is connected to the container. The accumulator apparatus is configured to switch between trapping sterilant fluid delivered into the device receiving area and delivering sterilant fluid to the device receiving area based on pressure changes in the device receiving area.

According to a further aspect, this disclosure provides a method of decontaminating a device such as a lumen device. The method includes the step of providing a device decontamination system, such as a lumen device decontamination system with a terminal package in fluid communication with an accumulator apparatus. Decontamination is performed within the terminal package by cycling between a first phase and a second phase. In the first phase, sterilant fluid is delivered from the accumulator apparatus by introducing a vacuum within the terminal package. In the second phase, sterilant fluid is drawn into the accumulator apparatus by injecting a sterilant fluid into the terminal package.

BRIEF DESCRIPTION OF THE DRAWINGS

The present disclosure will be described hereafter with reference to the attached drawings which are given as non-limiting examples only, in which:

FIGS. 3A-8B illustrate fluid flow in/out of the accumulator pump during various stages of a decontamination process.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

This disclosure relates to a decontamination system for decontaminating a device, such as a lumen device. In some embodiments, the system includes an accumulator pump that utilizes pressure changes during decontamination cycles to direct sterilant fluid into a device without having a direct connection with a motorized pump. This eliminates one or more connections traversing the sterile barrier of the terminal package, and reduces complexity of sterilizing the interior volume of the device. The accumulator pump could potentially be used with any sterilization or decontamination process that experiences pressure changes during the sterilization/decontamination cycle(s), including steam and ethylene oxide. In some cases, the accumulator pump could be a standalone device to generate turbulence inside a decontamination chamber or in a terminal package; this agitation can aid in achieving a better microbial kill on the outside of the device.

Figure 1:
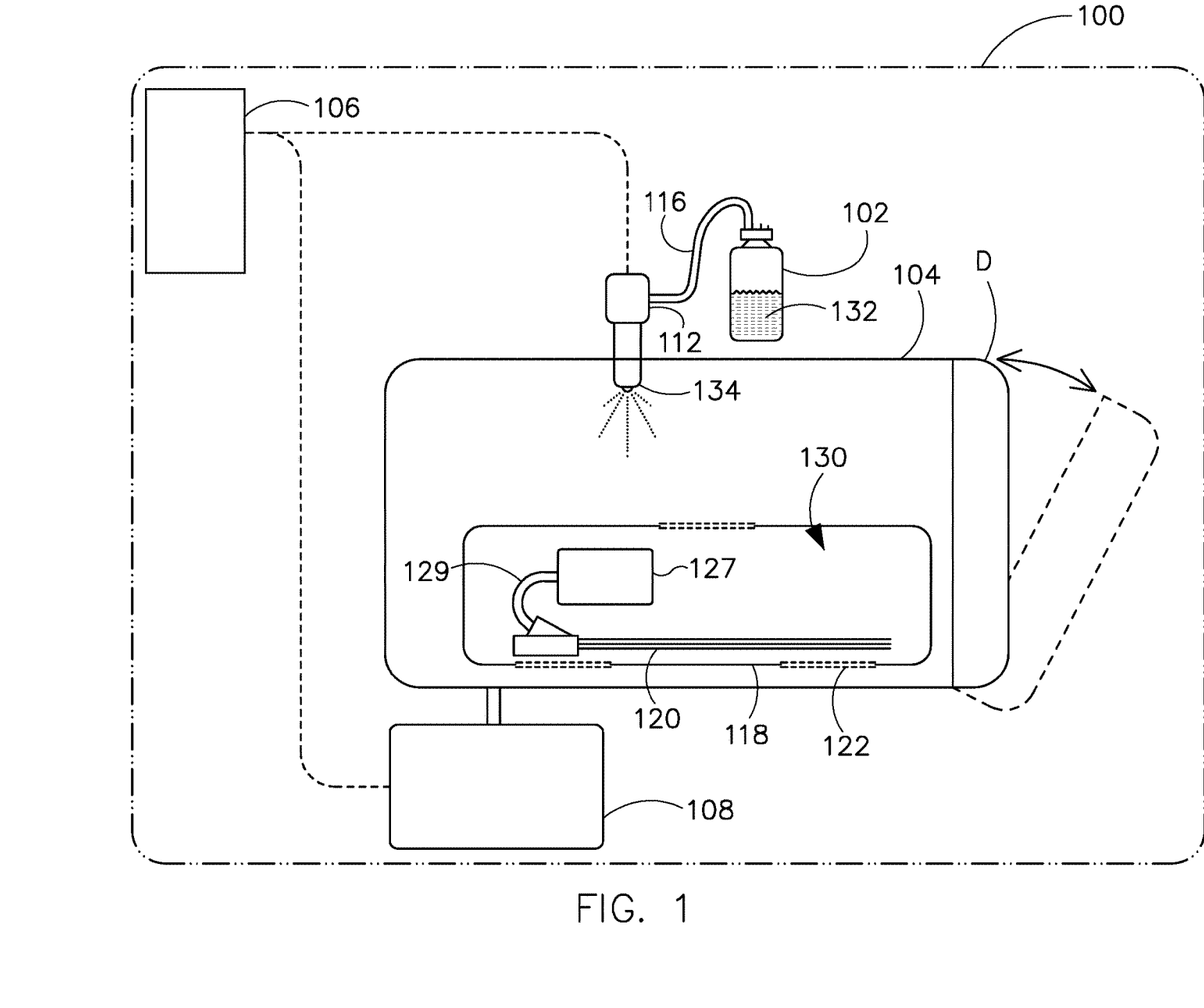
FIG. 1 is diagrammatic view of a system for decontaminating a medical device according to an embodiment of the present disclosure.

FIG. 1 is a diagrammatic view of one embodiment of a system 100 for decontaminating a medical, dental, or other device, which may have one or more lumens extending there-through. The system 100 includes a reservoir 102, a decontamination chamber 104, a system controller 106, an environmental monitoring and control system 108, and vaporizer 112 which is connected to the reservoir 102 by conduit 116. A terminal package 118 containing a device 120 for decontamination may be placed within the decontamination chamber 104. In the illustrated embodiment, the terminal package 118 includes a fluid inlet, which could be in the form of a plurality of openings or pores 122. The reservoir 102 may be in fluid communication with the decontamination chamber 104 via vaporizer 112. This provides sterilant fluid to an accumulator pump 127, which can deliver sterilant fluid to the device, such as into one or more lumens of the lumen device 120 via a fluid conduit 129 based on pressure changes in the surrounding environment in the terminal package 118. In the embodiment shown, the accumulator pump 127 allows sterilant fluid 132 to be directed into one or more lumens without having a direct connection between a motorized pump and the lumen device 120. In order words, sterilant fluid 132 is delivered to the device 120 in a conduit-free manner via vaporizer 112.

Depending on the circumstances, the accumulator pump 127 could be integral with the terminal package 118; in other embodiments, the accumulator pump 127 could be detachably mounted in the terminal package. Embodiments are also contemplated in which the accumulator pump 127 could be used to aid decontamination of external surfaces of the device 120. For example, the accumulator pump 127 could be positioned within the terminal package 118 or the decontamination chamber 104 without a connection to the device 120; in such embodiments, the accumulator pump 127 could be used to provide turbulence or agitation within the terminal package 120 and/or decontamination chamber 104.

The system controller 106 provides control signals to and/or receives condition sensing and equipment status signals from the reservoir 102, the decontamination chamber 104, environmental monitoring and control system 108, and/or the vaporizer 112. In some embodiments, the system 100 can be assembled in a device small enough to sit on a tabletop or counter. For example, the decontamination chamber 104 may have an interior volume of less than about ten cubic feet.

The device 120 to be decontaminated can be placed into the decontamination chamber 104 by opening the door D and placing the device 120 on a rack or other supporting assembly in the interior of the decontamination chamber 104. In some embodiments, the device 120 may be enclosed in the terminal package 118 before being placed in the decontamination chamber 104. In the example shown, the terminal package 118 defines a device receiving area 130, such as a lumen device receiving area, to receive the device 120, such as a lumen device, for decontamination. In the illustrated embodiment, the terminal package 118 includes a plurality of openings or pores 122.

The reservoir 102 may be a holding tank or other assembly configured to hold a sterilant fluid 132. In some embodiments, the sterilant fluid 132 can be a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemic al Indicators—Part I: General Requirements" (Arlington, Va.: AAMI 2005). In some embodiments, the sterilant fluid 132 can be a room temperature (e.g., 20° C. to 25° C.) substance that can be dispersed as a fluid, such as a liquid, a vapor, or a combination thereof (such as a fog) during the decontamination process. Suitable substances for the sterilant fluid 132 include hydrogen peroxide ($H_2O_2$) and peracetic acid (PAA).

In various embodiments, the sterilant fluid is a composition that includes: (a) hydrogen peroxide; (b) organic acid; (c) a polymeric sulfonic acid resin based chelator; and (d) surfactant. The composition includes less than about 1 wt. % of an anticorrosive agent. The composition can further optionally include water.

In one aspect, the hydrogen peroxide present in the composition can be from about 0.5 wt. % to about 30 wt. %, from about 0.5 wt. % to about 1.5 wt. %, from about 0.8 wt. % to about 1.2 wt. %, from about 20 wt. % to about 30 wt. % and all ranges and values from about 0.5 wt. % to about 30 wt. %.

In another aspect, the acetic acid present in the composition can be from about 1 wt. % to about 25 wt. %, from about 4 wt. % to about 20 wt. %, from about 4.5 wt. % to about 5.5 wt. %, from about 9 wt. % to about 17 wt. % and all ranges and values from about 1 wt. % to about 25 wt. %.

In still another aspect, the peracetic acid present in the composition can be from about 0.01 wt. % to about 25 wt. %, from about 0.05 wt. % to about 20 wt. %, from about 0.05 wt. % to about 0.1 wt. %, from about 3.5 wt. % to about 8 wt. % and all ranges and values from about 0.01 wt. % to about 25 wt. %.

In yet another aspect, the polymeric resin chelator present in the composition can be from about 0.1 wt. % to about 5 wt. %, from about 0.2 wt. % to about 2 wt. %, from about 0.5 wt. % to about 1.5 wt. % and all ranges and value from about 0.1 wt. % to about 5 wt. %.

In various embodiments, the present invention provides for a composition that includes: (a) hydrogen peroxide, present in a concentration of about 0.5 wt. % to about 30 wt. %, e.g., about 28 wt. %; (b) acetic acid, present in a concentration of about 3 wt. % to about 25 wt. %, e.g., about 16 wt. %; (c) a sulfonic acid supported polymeric resin chelator present in a concentration of about 0.1 wt. % to about 5 wt. %, e.g., about 0.2 wt. % to about 0.7 wt. %; and, optionally, (d) Pluronic® 10R5 surfactant block copolymer, present in a concentration of about 2.0 wt. %, wherein the composition comprises less than about 0.1 wt. % of an anticorrosive agent, e.g., 0 wt. % of an anticorrosive agent. The composition can further optionally include water. In some embodiments, the hydrogen peroxide and acetic acid can combine to form peracetic acid, present in about 4 wt. % to about 8 wt. %, e.g., 6.8-7.5 wt. %.

In certain aspects, the peracetic acid/hydrogen peroxide compositions are stabilized without the need for a phosphonic based chelator, such as 1-hydroxyethylidene-1,1,-diphosphonic acid. In other aspects, a phosphonic based chelator, such as 1-hydroxyethylidene-1,1,-diphosphonic acid can be included in the sterilant fluid and therefore, component c), the polymeric sulfonic acid resin is optional.

The use of the polymeric stabilizer is detailed in pending PCT application PCT/US19/53090, filed Sep. 26, 2019, entitled "Peracetic Acid Stabilized Compositions with Polymeric Resins Chelators", the contents of which are incorporated herein by reference.

The terminal package 118 is sized so that the device 120 to be decontaminated fits within the terminal package 118. In some embodiments, the terminal package 118 may be generally described as having a top, a bottom, and four sides extending between the top and bottom to create a cube-like structure. However, the terminal package 118 may have any suitable shape which encloses the device 120. In some embodiments, the terminal package 118 may be formed from a rigid material such that the terminal package 118 has a rigid or structured shape. Alternatively, the terminal package 118 may be formed from a flexible material such that the terminal package 118 has a flexible shape. Suitable materials for the terminal package 118 include but are not limited to a polymeric non-woven sheet, such as spun-bonded polyethylene (e.g., Tyvek®, sold by E.I. du Pont de Nemours and Company, Wilmington, Del.), and polymeric materials such as polyester and polypropylene. Suitable materials for terminal package 118 having a rigid or structured shape include but are not limited to various metals such as aluminum, stainless steel and/or various polymers in rigid form such as polyethylene and/or polypropylene.

The device 120 may be positioned within the terminal package 118 and subjected to one or more decontamination cycles. Suitable devices include any medical, dental or other device, including those having at least one lumen extending through at least a portion of the device. In some embodiments, the device 120 may include at least one lumen extending the entire length of the device. For example, the device 120 may be an endoscope.

The terminal package 118 may be configured to prevent or reduce microbes and/or other contaminants from entering the terminal package 118. In some embodiments, for example, the terminal package 118 can include a material suitable for allowing flow of a sterilant fluid, such as hydrogen peroxide ($H_2O_2$) and/or peracetic acid (PAA), into the device receiving area 130 of the terminal package 118 and blocking or reducing the flow of contaminants into the interior of the terminal package 118. In the illustrated embodiment, the terminal package 118 includes a plurality of openings or pores 122 for allowing flow of the sterilant fluid 132 into the terminal package 118. In some embodiments, the pores 122 may be sized so as to allow the sterilant fluid 132 and/or air to communicate into and out of the container 118 as well as prevent microbes from entering the terminal package 118.

In some embodiments, the sterilant fluid 132 can flow from the reservoir 102 to vaporizer 112 and subsequently to decontamination chamber 104 and device 120. The sterilant fluid 132 from vaporizer 112 may decontaminate the internal surfaces of the device's 120 port via the accumulator pump 127. As shown, the accumulator pump 127 may be connected with one or more lumens of the device 120 to deliver sterilant fluid. In other embodiments, the accumulator pump 127 could be a standalone device in the terminal package 118 or decontamination chamber 104, without connection to the device 120, to create turbulence or agitation, which aids in decontaminating external surfaces of the device 120. The amount of sterilant fluid 132 introduced into the decontamination chamber 104, the device 120 or a combination thereof can be controlled by the system controller 106 by controlling the amount of the sterilant fluid 132 fed or delivered to vaporizer 112. The rate and amount of the sterilant fluid 132 delivered to vaporizer 112 may be preprogrammed into the system controller 106 or may be manually entered into the system controller 106 by a user of the system 100.

To decontaminate a device, such as a medical, dental or other device, the device 120 may be sealed within the terminal package 118 and placed in the decontamination chamber 104. The device 120 is then subjected to a decontamination process which may include one or more decontamination cycles. A suitable cycle may include adjusting the pressure of the decontamination chamber 104 to a suitable range, such as to a pressure less than 10 Torr, conditioning using plasma, and introducing the sterilant fluid 132 into the decontamination chamber 104 via vaporizer 112 and nozzle 134. The sterilant fluid 132 may be held within the decontamination chamber 104 for a period of time to facilitate the decontamination of the device 120, and in particular, the exterior surfaces of the device 120. Similarly, the sterilant fluid 132 may be held within the device 120 for a period of time to facilitate the decontamination of the interior surfaces or lumen(s) of the device 120. When the sterilant fluid 132 has been held in the decontamination chamber 104 for the desired or programmed amount of time, the system controller 106 can vent the decontamination chamber 104 to a higher, but sub-atmospheric pressure. The system controller 106 can then hold the pressure within the decontamination chamber 104 for a period of time to further facilitate the decontamination of the load. Following the hold period, the system controller 106 may evacuate the decontamination chamber 104 to remove the sterilant fluid residuals from the decontamination chamber 104 which may also include a plasma treatment to further enhance the removal of the substance residuals, followed by venting the decontamination chamber 104. This cycle or steps may be repeated or extended as part of a comprehensive cycle. As the process cycles, and the pressure changes within the decontamination chamber 104, the accumulator pump 127 traps sterilant fluid and directs this into one or more lumens of the device 120. The stages of the decontamination process, and corresponding cycles of trapping and venting sterilant fluid by the accumulation pump 127, are discussed below with reference to FIGS. 3A-8B.

Figure 2:
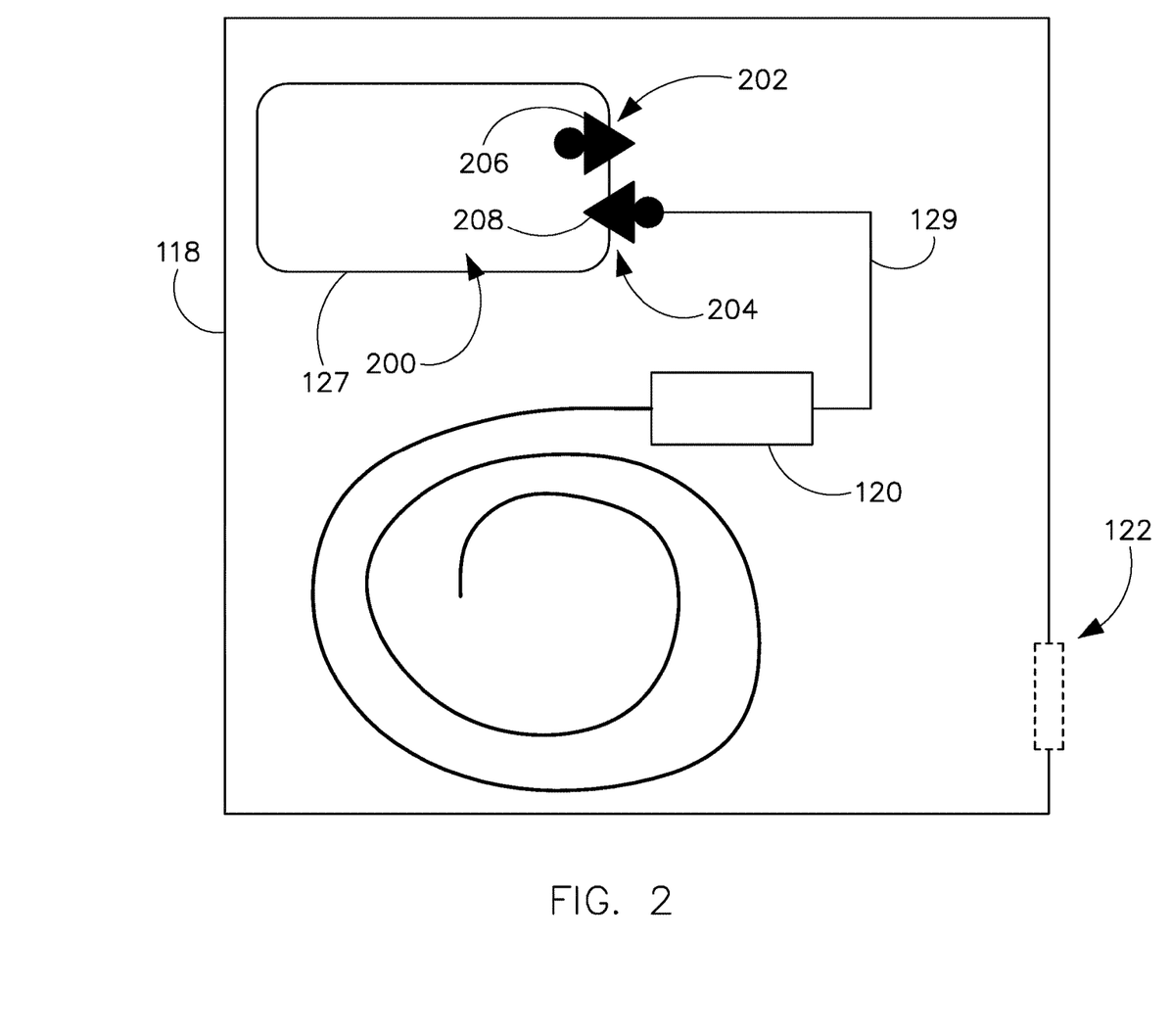
FIG. 2 is a side diagrammatic view of an example terminal package with an accumulator pump according to an embodiment of the present disclosure.

FIG. 2 is a diagrammatical view of the terminal package 118 with an accumulator pump 127 fluidly connected with the device 120 via the fluid conduit 129 according to an embodiment of this disclosure. The accumulator pump 127 works by utilizing pressure changes to trap sterilant fluid for use when the pressure outside of the accumulator pump 127 decreases. The greater the pressure changes, the larger the volume of sterilant fluid trapped and delivered.

In the embodiment shown, the accumulator pump 127 defines an accumulator reservoir 200, which is a cavity dimensioned to trap a volume of sterilant fluid. As shown, the accumulator reservoir 200 includes an inlet 202 that provides fluid communication between the accumulator reservoir 200 and interior of the terminal package 118; an outlet 204 provides fluid communication between the accumulator reservoir 200 and the device 120 via the fluid conduit 129. In the embodiment shown, a first check valve 206 provides one-way flow through the inlet 202 into the accumulator reservoir 200 from the interior of the terminal package 118 and prevents flow out of the accumulator reservoir 200 through the inlet 202. As shown, a second check valve 208 provides one-way flow out of the outlet 202 from the accumulator reservoir 200 into the device 120 through the fluid conduit 129 and prevents flow out of the accumulator reservoir 202 through the outlet 204. The accumulator pump 127 could be formed from a variety of sterilant-compatible materials, including but not limited to stainless steel, aluminum, polypropylene, polytetrafluoroethylene (PTFE), polyethylene and high density polyethylene (HDPE) and/or fluorinated ethylene propylene (FEP).

Although the inlet 202 and the outlet 204 are shown as separate openings in this embodiment, there are embodiments contemplated in which the inlet 202 and outlet 204 could be formed from a single opening. For example, depending on the circumstances, the accumulator reservoir 200 could have a single opening with fluid flowing in and out of accumulator reservoir 202 based on pressure changes within the surrounding decontamination chamber 104. This may be beneficial for greater exposure of the sterilant fluid in the one of more lumens of the device 120.

FIGS. 3A-8B illustrate cycles during an example decontamination process and corresponding flow of sterilant fluid into/out of the accumulator pump 127. FIGS. 3A, 4A, 5A, 6A, 7A, and 8A, illustrate sterilant fluid flow into/out of the accumulator pump 127 during the example decontamination process. FIGS. 3B, 4B, 5B, 6B, 7B, and 8B are charts showing pressure variations within the decontamination chamber 104 during various cycles of the example decontamination process corresponding with FIGS. 3A, 4A, 5A, 6A, 7A, and 8A, respectively. The pressure (torr) is shown along the Y-axis and corresponding time during the decontamination process is shown along the X-axis.

Figure 3A:
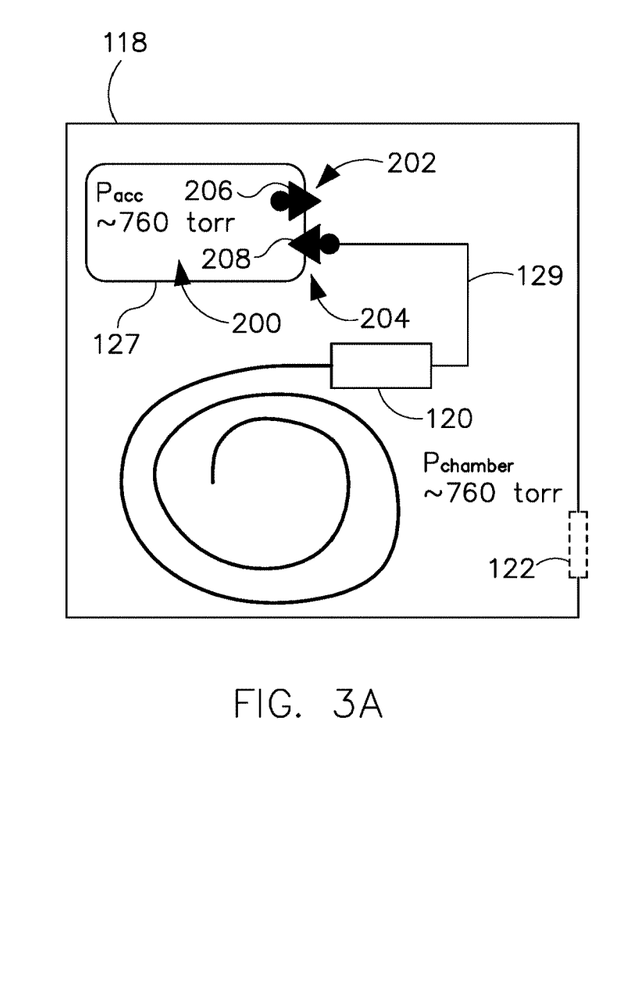
Figure 3B:
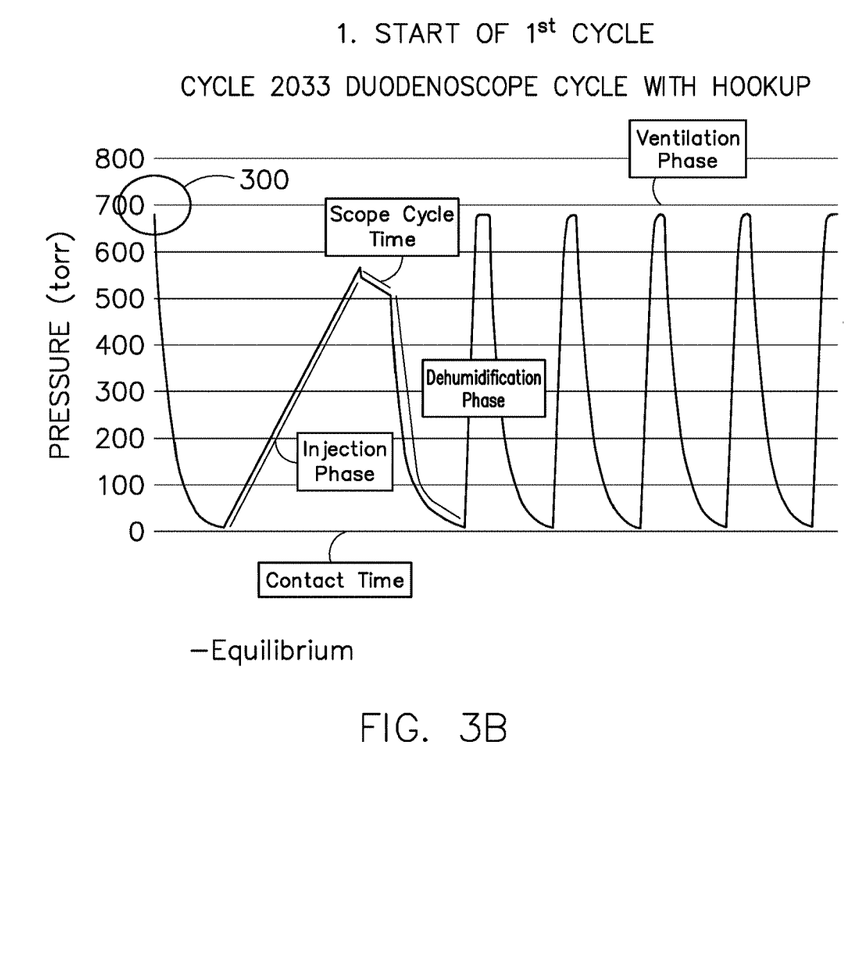

FIGS. 3A and 3B illustrate the decontamination system 100 prior to the start of a decontamination cycle. FIG. 3A shows there is equilibrium between the pressure within the accumulator reservoir 200 and the surrounding pressure in the terminal package 118. The pressure within the accumulator reservoir 200 and surrounding environment at this stage is shown at about 760 torr for purposes of example, but other pressures could be possible at equilibrium depending on the circumstances. The pressure at this point in the decontamination cycle is shown at 300 in FIG. 3B.

Figure 4A:
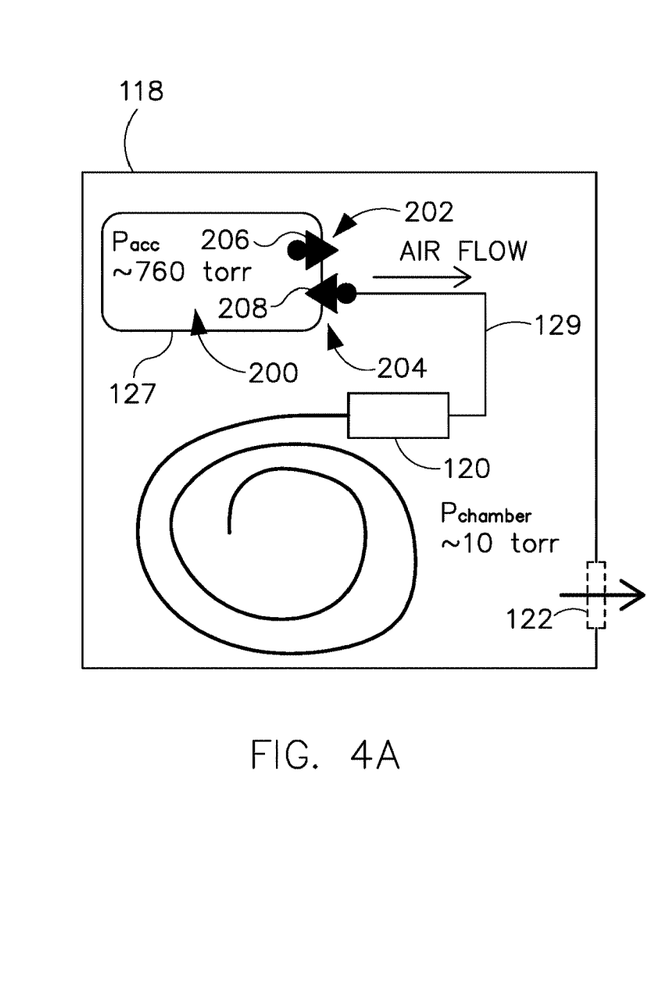
Figure 4B:
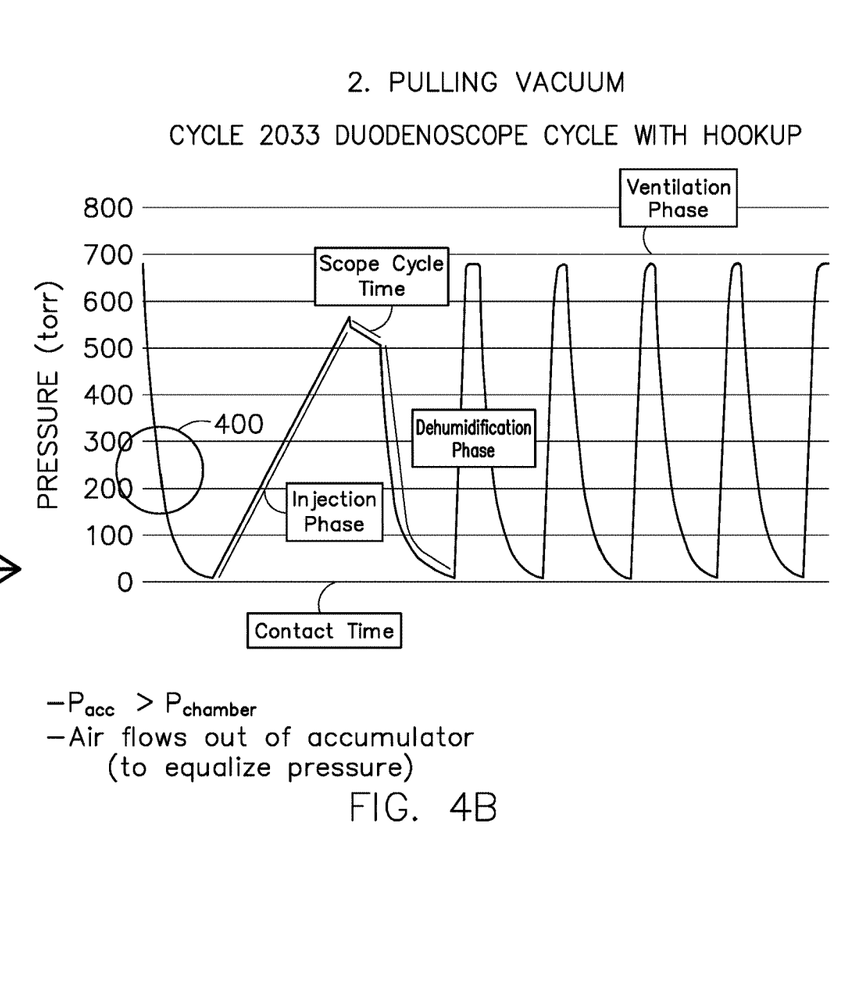

When the decontamination process begins in the embodiment shown, the system 100 introduces a drop in pressure within the decontamination chamber 104 as illustrated by FIGS. 4A and 4B. FIG. 4A shows for purposes of example that the pressure at this stage could be approximately 760 torr within the accumulator reservoir 200 while the pressure of the surrounding environment could be approximately 10 torr. This pressure drop causes air within the accumulator reservoir 200 to flow out of the outlet 204 through the device 120. An example pressure at this point in the decontamination cycle is shown at 400 in FIG. 4B.

Figure 5A:
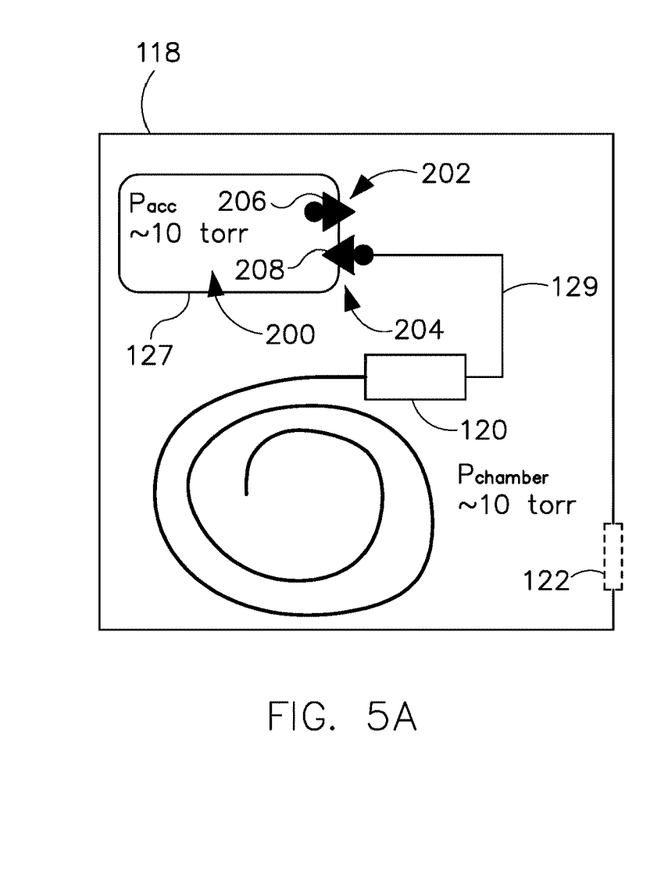
Figure 5B:
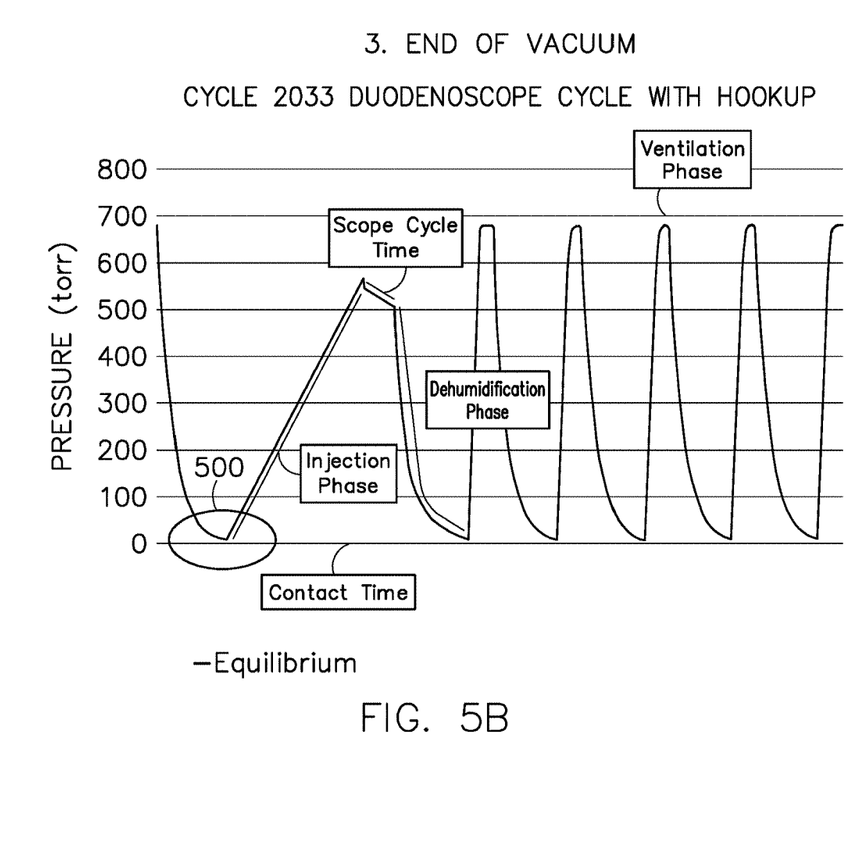

Air continues to flow out of the accumulator pump 127 until pressure within the accumulator reservoir 200 equalizes with the surrounding environment. FIG. 5A shows for purposes of example that the pressure at equilibrium could be approximately 10 torr in the accumulator reservoir 200 and the surrounding environment. The equilibrium point at this stage in the decontamination cycle is shown at 500 in FIG. 5B.

Figure 6A:
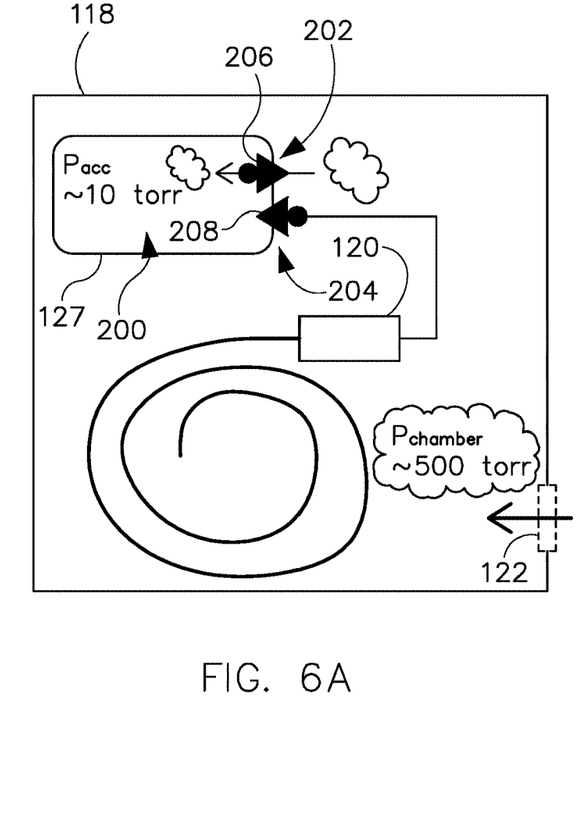
Figure 6B:
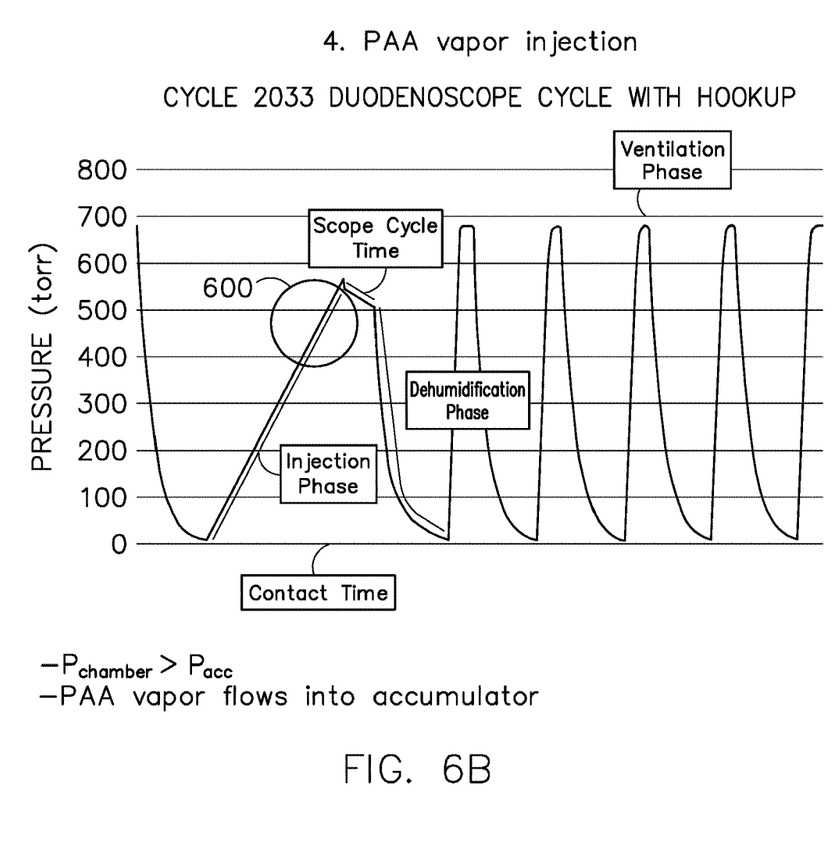

Next, the decontamination process enters an injection phase in which sterilant fluid, such as peracetic acid (PAA), is introduced into the decontamination chamber 104. The injection of sterilant fluid into the decontamination chamber 104 introduces sterilant fluid through the plurality of pores 122 of the terminal package 118, which increases pressure in the terminal package 118 surrounding the accumulator pump 127. This increase in pressure causes sterilant fluid to flow into the accumulator reservoir 200 through the inlet 202. Due to the first check valve 206, which provides a one-way flow, the sterilant fluid is trapped within the accumulator reservoir 200. The sterilant fluid does not flow out of the outlet 204 at this stage because the pressure within the accumulator reservoir 200 is lower than the surrounding environment. FIG. 6A shows for purposes of example that the pressure during the injection phase could be approximately 10 torr in the accumulator reservoir 200 and approximately 500 torr in the surrounding environment. The pressure at this stage in the decontamination cycle is shown at 600 in FIG. 6B.

Figure 7A:
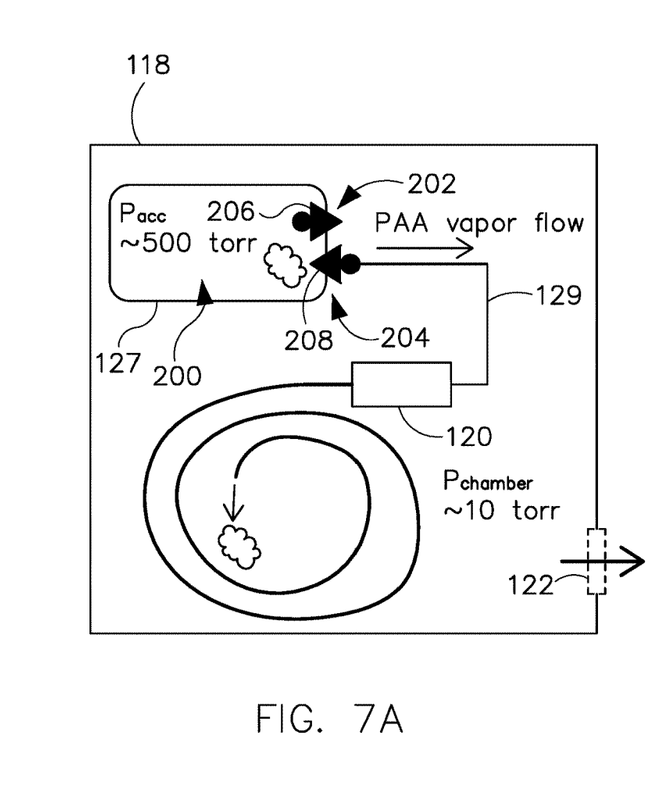
Figure 7B:
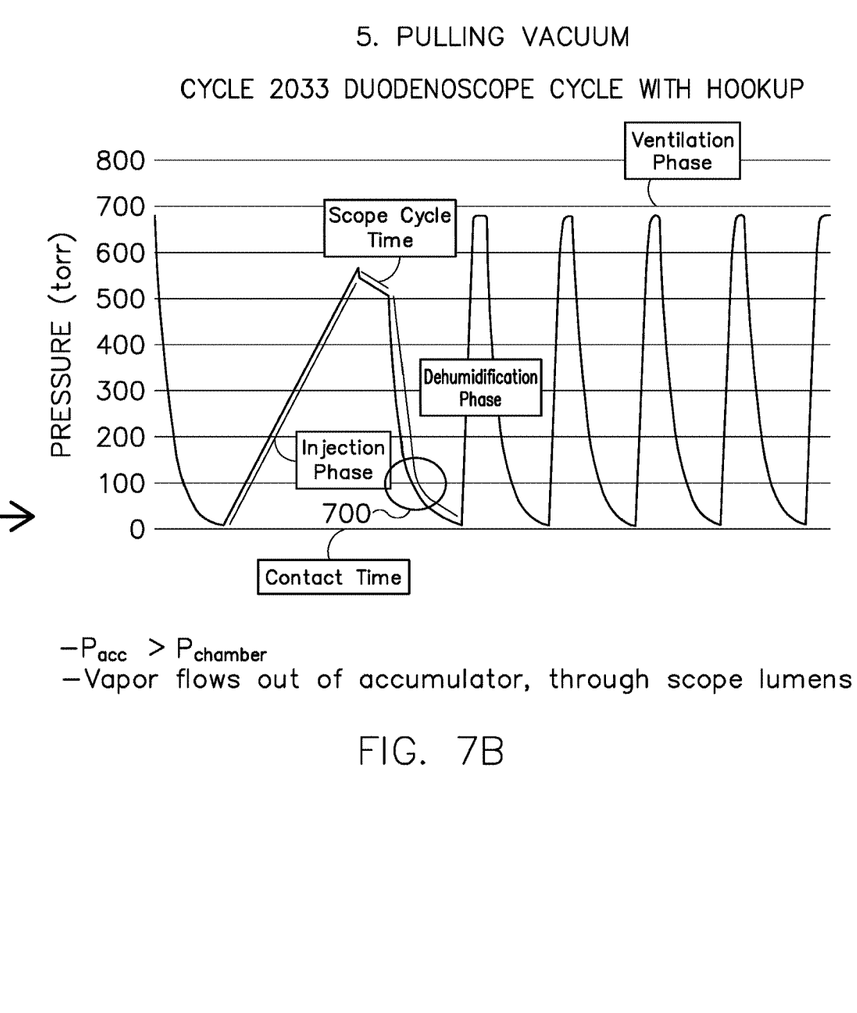

The next stage in the decontamination process in the embodiment shown introduces a pressure drop within the decontamination chamber 104 as illustrated by FIGS. 7A and 7B. FIG. 7A shows for purposes of example that the pressure at this stage could be approximately 500 torr within the accumulator reservoir 200 while the pressure of the surrounding environment could be approximately 10 torr. This pressure differential causes sterilant fluid trapped within the accumulator reservoir 200 to flow out of the outlet 204 through the device 120. An example pressure at this point in the decontamination cycle is shown at 700 in FIG. 7B.

Figure 8A:
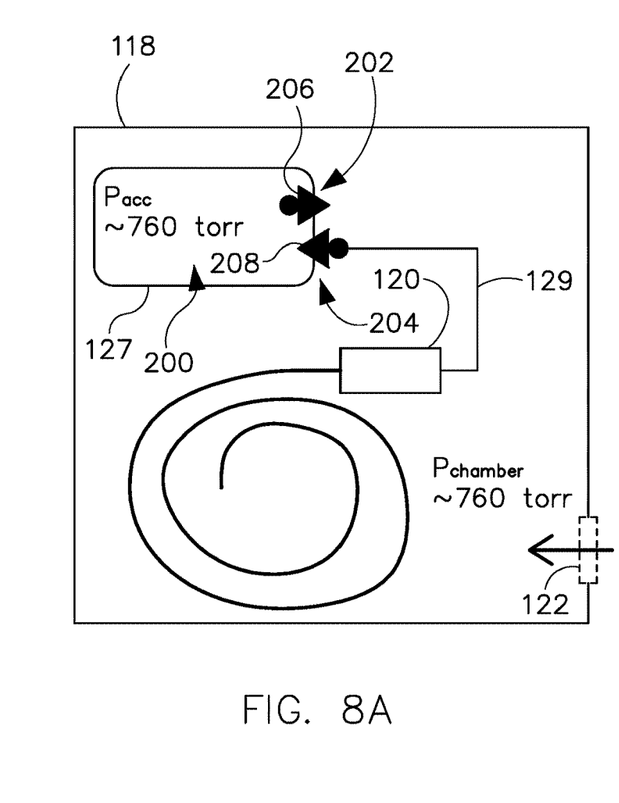
Figure 8B:
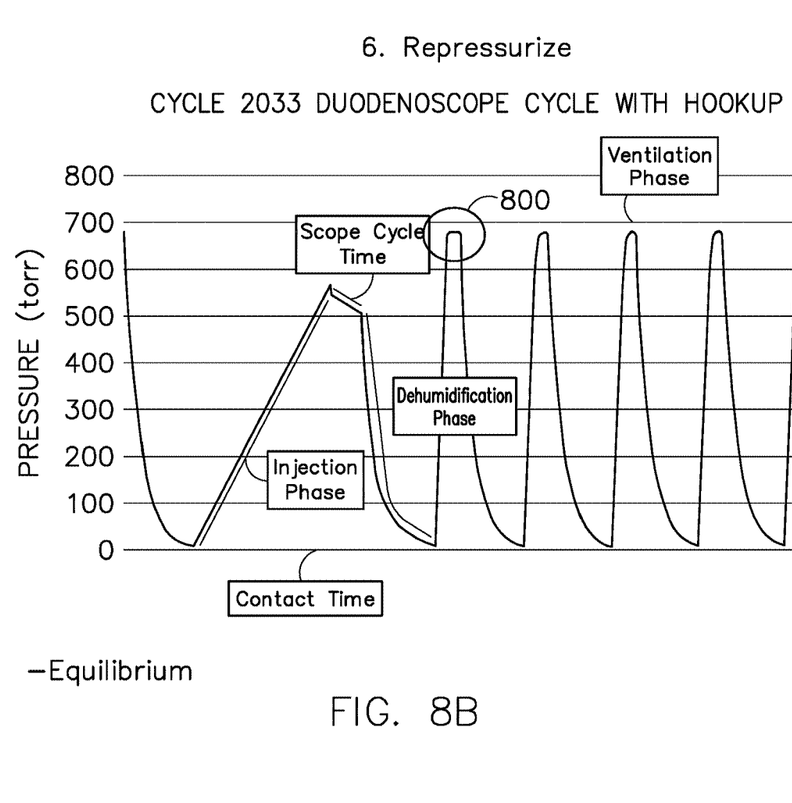

Sterilant fluid continues to flow out of the accumulator pump 127 until pressure within the accumulator reservoir 200 equalizes with the surrounding environment. FIG. 8A shows for purposes of example that the pressure at equilibrium could be approximately 760 torr in the accumulator reservoir 200 and the surrounding environment at this stage in the decontamination process. The equilibrium point at this stage is shown at 800 in FIG. 8B. These cycles or steps may be repeated or extended as part of a comprehensive decontamination cycle in which sterilant fluid is trapped in the accumulator reservoir 200 and then vented into the device 120.

EXAMPLES

Illustrative examples of the method and system disclosed herein are provided below. An embodiment of the method and system may include any one or more, and any combination of, the examples described below.

Example 1 is a decontamination system for a device, such as a lumen device. The decontamination system includes a terminal package defining a device receiving area, such as a lumen device receiving area. The terminal package includes a fluid inlet through which sterilant fluid can be delivered to the device receiving area. The system includes an accumulator apparatus configured to switch between trapping sterilant fluid delivered into the device receiving area and delivering sterilant fluid to the device receiving area based on pressure changes in the device receiving area.

In Example 2, the subject matter of Example 1 is further configured such that the accumulator apparatus is integral with the device container.

In Example 3, the subject matter of Example 2 is further configured to include a motorized pump in fluid communication with the device receiving area such that the accumulator apparatus is configured to deliver sterilant fluid to the device receiving area through a flow path separated from a flow path of the motorized pump.

In Example 4, the subject matter of Example 2 is further configured such that the accumulator apparatus includes an accumulator reservoir in fluid communication with the device receiving area.

In Example 5, the subject matter of Example 4 is further configured to include a decontamination chamber dimensioned to receive the terminal package such that sterilant fluid delivery from the decontamination chamber to the terminal package is conduit-free.

In Example 6, the subject matter of Example 5 is further configured to include a first one-way valve configured to allow flow into the accumulator reservoir from the device receiving area through the inlet, but prevent flow from the accumulator reservoir into the device receiving area through the inlet.

In Example 7, the subject matter of Example 6 is further configured to include a second one-way valve configured to allow flow into the device receiving area from the accumulator reservoir through the outlet, but prevent flow from the device receiving area into the accumulator reservoir through the outlet.

Example 8 is a terminal package for use in a decontaminating system. The terminal package includes a container dimensioned to receive a device, such as a lumen device, such that the container defines a device receiving area. The container includes a fluid inlet defined in the container to deliver a sterilant fluid to the device receiving area. An accumulator apparatus is provided that is connected to the container. The accumulator apparatus is configured to switch between trapping sterilant fluid delivered into the device receiving area and delivering sterilant fluid to the device receiving area based on pressure changes in the device receiving area.

In Example 9, the subject matter of Example 8 is further configured such the accumulator apparatus includes an accumulator reservoir in fluid communication with the device receiving area.

In Example 10, the subject matter of Example 9 is further configured such that the accumulator reservoir includes an inlet and an outlet in fluid communication with the device receiving area.

In Example 11, the subject matter of Example 10 is further to include a first one-way valve configured to allow flow into the accumulator reservoir from the device receiving area through the inlet, but prevent flow from the accumulator reservoir into the device receiving area through the inlet.

In Example 12, the subject matter of Example 11 is further configured to include a second one-way valve configured to allow flow into the device receiving area from the accumulator reservoir through the outlet, but prevent flow from the device receiving area into the accumulator reservoir through the outlet.

In Example 13, the subject matter of Example 8 is further configured such that the accumulator apparatus is integral with the container.

In Example 14, the subject matter of Example 13 is further configured such that the accumulator apparatus is in fluid communication with the fluid connector.

In Example 15, the subject matter of Example 14 is further configured such that the accumulator apparatus is constructed from one or more of stainless steel, aluminum, polypropylene, polytetrafluoroethylene (PTFE), polyethylene and high density polyethylene (HDPE) and/or fluorinated ethylene propylene (FEP).

Example 16 is a method of decontaminating a device, such as a lumen device. The method includes the step of providing a device decontamination system, such as a lumen device decontamination system, with a terminal package in fluid communication with an accumulator apparatus. Decontamination is performed within the terminal package by cycling between a first phase and a second phase. In the first phase, sterilant fluid is delivered from the accumulator apparatus by introducing a vacuum within the terminal package. In the second phase, sterilant fluid is drawn into the accumulator apparatus by injecting a sterilant fluid into the terminal package.

In Example 17, the subject matter of Example 16 is further configured such that the accumulator apparatus is integral with the terminal package.

In Example 18, the subject matter of Example 17 is further configured such that the accumulator apparatus has an accumulator reservoir including an inlet and an outlet.

In Example 19, the subject matter of Example 18 is further configured such that the accumulator apparatus includes a first one-way valve configured to allow flow into the accumulator reservoir through the inlet, but prevent flow from the accumulator reservoir through the inlet.

In Example 20, the subject matter of Example 19 is further configured such that the accumulator apparatus includes a second one-way valve configured to allow flow from the accumulator reservoir through the outlet, but prevent flow into the accumulator reservoir through the outlet.

Although the present disclosure has been described with reference to particular means, materials and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A decontamination system for a device, the decontamination system comprising:
    a terminal package defining a device receiving area, wherein the terminal package includes a fluid inlet through which sterilant fluid can be delivered to the device receiving area;
    an accumulator apparatus comprising an accumulator reservoir in fluid communication with the device receiving area comprising an inlet and an outlet in fluid communication with the device receiving area, further comprising a first one-way valve configured to allow flow into the accumulator reservoir from the device receiving area through the inlet, but prevent flow from the accumulator reservoir into the device receiving area through the inlet and configured to switch between trapping sterilant fluid delivered into the device receiving area and delivering sterilant fluid to the device receiving area based on pressure changes in the device receiving area wherein the accumulator apparatus is integral with the device receiving area; and
    a decontamination chamber dimensioned to receive the terminal package, wherein sterilant fluid delivery from the decontamination chamber to the terminal package is conduit-free.

2. The decontamination system of claim 1, further comprising a motorized pump in fluid communication with the device receiving area, wherein the accumulator apparatus is configured to deliver sterilant fluid to the device receiving area through a flow path separated from a flow path of the motorized pump.

3. The decontamination system of claim 1, further comprising a second one-way valve configured to allow flow into the device receiving area from the accumulator reservoir through the outlet, but prevent flow from the device receiving area into the accumulator reservoir through the outlet.

\* \* \* \* \*